United States Patent [19]

Nazarenko

[11] 4,251,468
[45] Feb. 17, 1981

[54] RECOVERY OF TRIARYLBORANES

[75] Inventor: Nicholas Nazarenko, Orange, Tex.

[73] Assignee: E. I. Du Pont de Nemours and Company, Wilmington, Del.

[21] Appl. No.: 106,251

[22] Filed: Dec. 21, 1979

[51] Int. Cl.$^3$ ............................................... C07F 5/02
[52] U.S. Cl. ....................................................... 568/1
[58] Field of Search .................................. 260/606.5 B

[56] References Cited

U.S. PATENT DOCUMENTS

| | | | |
|---|---|---|---|
| 3,090,801 | 5/1963 | Washburn et al. | 260/502.3 X |
| 4,045,495 | 8/1977 | Nazarenko et al. | 260/606.5 B |
| 4,046,815 | 9/1977 | Nazarenko | 260/606.5 B |
| 4,076,756 | 2/1978 | Nazarenko et al. | 260/606.5 B |
| 4,082,811 | 4/1978 | Shook | 260/606.5 B |
| 4,134,923 | 1/1979 | Reimer | 260/606.5 B |
| 4,177,215 | 12/1979 | Seidel | 260/606.5 B |

*Primary Examiner*—Helen M. S. Sneed

[57] ABSTRACT

Triphenylborane is recovered from solutions of its alkali metal adduct by neutralization with carbon dioxide.

6 Claims, No Drawings

RECOVERY OF TRIARYLBORANES

BACKGROUND OF THE INVENTION

1. Field of the Invention

The present invention is directed to the recovery of triarylboranes and more particularly to the recovery of triphenylborane by the neutralization of its alkali metal adduct with carbon dioxide.

2. Description of the Prior Art

Organoboranes have been produced by a variety of methods including the Grignard reaction and more recently by the reaction of an alkali metal, an organohalide and an orthoborate ester.

U.S. Pat. No. 3,090,801 issued on May 21, 1963 to Washburn et al. discloses processes which purport to produce mono, di and trisubstituted boranes in high yields but the patentee's only disclosure of a method for recovery of the boranes is found in the examples. In Example 1 of the U.S. Pat. No. 3,090,801 patent, the reaction mixture is treated with methanol and water to hydrolize the dimethylboronate to produce the acid form. After the acid form is obtained, the mixture is then distilled to remove xylene, methanol and side reaction products. In Examples 2 and 3, the patentee purports to recover the acid form of the borane by contacting the reaction product with an aqueous solution containing concentrated sulfuric acid followed by extraction or distillation. Thee recovery procedures are not satisfactory for the trisubstituted boranes because the trisubstituted boranes are relatively unstable and readily degrade in the presence of water and/or acid especially at elevated temperatures.

Substantial improvements in the preparation of triaryl substituted boranes are disclosed in U.S. Pat. Nos. 4,046,815; 4,045,495; and 4,076,756, issued on Sept. 6, 1977; Aug. 30, 1977 and Feb. 28 1978, respectively, all assigned to E. I. du Pont de Nemours and Company. These improvements involve reacting an alkali metal, an organohalide, e.g., chlorobenzene and an orthoborate ester, e.g., triisopropylorthoborate in an inert organic solvent such as cyclohexane. The reaction product is contacted with water to form the stable salt or adduct of the trisubstituted borane. Since the salt or adduct is a relatively stable form of the borane, alcohol can be removed by distillation without excessively degrading the borane which can then be recovered in free form by neutralizing the salt or adduct with a mineral acid to a pH not less than about 6.0 whereupon the trisubstituted borane precipitates from the solution. Neutralization is conducted so that a relatively pure trisubstituted product is obtained in good yield. The major impurity formed along with the trisubstituted borane in this improved process is the disubstituted borane, i.e., borinic acid. Lesser amounts of mono and tetrasubstituted boranes are also produced. Under optimum conditions the amount of disubstituted borinic acid is insufficient to coprecipitate with trisubstituted borane because the disubstituted borinic acid remains in solution and the autocatalytic degradation of the trisubstituted borane by that acid does not occur to any significant degree. Neutralization with known compounds, e.g., mineral acids, wherein relatively large amounts of diphenyl borinic acid are present, i.e., where the ratio of the trisubstituted borane to the disubstituted borane is less than about 13/1, to maximize recovery of the trisubstituted borane can result in coprecipitation of the borinic acid and concomitant degradation of the trisubstituted product. It has been suggested that the coprecipitation can be avoided by diluting the salt solution with water to avoid precipitation of the disubstituted borane, however, the handling of this additional water increases the complexity and the cost of recovery.

Another method for maximizing recovery of trisubstituted borane of acceptable purity in the presence of borinic acid involves conducting the neutralization to a pH not lower than a certain value while maintaining a specified minimum ionic concentration in the solution. The trisubstituted boranes will precipitate from an aqueous solution at a higher pH than the disubstituted borinic acid and the higher ionic strength favors the precipitation of the trisubstituted borane.

The preferred process for preparing the alkali metal hydroxide salt or adduct of the triarylborane to which the present invention can be applied involves reacting a finely divided alkali metal such as lithium, potassium, etc., but preferably sodium with an organohalide such as an aryl halide, e.g., chlorobenzene, and an orthoborate ester derived from secondary alkyl alcohol, e.g., isopropanol and sec-butanol in an inert organic solvent at a temperature in the range 15°–120° C.

The organohalide can be any halogen substituted aryl halide wherein the aryl group has 6–10 carbon atoms. Examples of suitable compounds include chlorobenzene, bromobenzene, chlorotolune, chloroaniline and the like. The amount of organohalide can vary depending upon its reactivity but preferably is maintained at a molar ratio in the range 3.5/1–3/1 with respect to the ester in the process where the reactants are contacted simultaneously.

The orthoborate esters which are suitable for reaction include those derived from an alcohol containing 1–10 carbon atoms which is represented by the formula $B(OR)_3$ wherein R is an alkyl group such as methyl, ethyl, isopropyl, etc. wherein the R's may be same or different. Preferred esters are those derived from secondary alcohols having 3–10 carbon atoms when used in conjunction with a cyclohexane solvent. Suitable solvents are those which are substantially inert with respect to the reactants and preferably exhibit a boiling point near atmospheric pressure to facilitate the removal of heat from the reaction. Examples of suitable solvents singly or in combination are branched or unbranched hydrocarbons having 5–10 carbon atoms, e.g., alkanes such as pentane, hexane, octane and 3-methyl pentane; cyclohexane, cyclooctane, cyclopentane; alkenes and cycloalkenes wherein the unsaturation does not react with the alkali metal, the organohalide or the orthoester. Such unsaturated solvents include hexene and octene. Useful aromatic hydrocarbons include xylene, benzene and the like.

After the reaction is complete, the reaction mixture is contacted with water, whereupon the alkali metal hydroxide salt, i.e., the adduct of the triarylborane is formed along with the salts of the under or over phenylated boron compounds, e.g., diphenyl borinic acid. Since the salts are stable in the aforementioned solution, volatile compounds which interfere with recovery of the trisubstituted boranes can be removed without excessive degradation of the borane. A suitable method for removal of such compounds, e.g., alcohol, is distillation. After removal of the volatile compounds, the trisubstituted adduct is neutralized according to the process of the present invention.

The triarylboranes which can be recovered according to the process of the present invention include those of the formula $R_3$-B wherein R is an aryl or substituted aryl group having 6-12 carbon atoms, e.g., phenylorthotolyl, paratolyl, naphthyl, methoxparaphenyl, para-aminophenyl, biphenyl, chlorophenyl and bromophenyl. Separation of triaryl borane from diaryl borinic acid is of particular interest although the mono and tetrasubstituted boranes wherein the aryl substituent groups are as described above can also be present.

In one embodiment the neutralization is accomplished by passing gaseous carbon dioxide through an aqueous or organic solution of the alkali metal hydroxide adduct or salt of the trisubstituted borane, preferably while the solution is at ambient temperature and atmospheric pressure. Temperature and pressure for the neutralization can be varied over a wide range depending in part upon the reactants, solvent, equipment, etc. with the caution that the degradation of the trisubstituted borane increases with increasing temperature especially in the presence of water.

It is preferred to introduce the carbon dioxide into a solution of the adduct which is initially free of solids to minimize contamination of the desired product. Solids, i.e., bicarbonates which are formed from and can be precipitated during the neutralization of the adduct and any excess base which is present from the reaction in which the trisubstituted borane was formed can be removed by washing the solid borane product with a solvent for the bicarbonates, e.g., water. Maintaining the excess base at the lowest practical level will minimize the formation of bicarbonate solids as will minimizing the ionic strength of the solution by any neutral compounds, e.g., sodium chloride.

The neutralization can also be conducted in a nonaqueous medium. In this embodiment of the present invention, the solid, trisubstituted borane adduct can be obtained in a reasonably pure form by evaporating aqueous solution thereof and, thereafter dissolving the solid trisubstituted borane adduct in an organic, nonreactive solvent. Such solvents include nitriles such as 3-pentenenitrile and butanes such as dicyanobutane. Examples of other suitable solvents include ketones such as acetone, and ethers such as tetrahydrofuran. The carbon dioxide can be introduced into the organic solvent under the conditions described above for the neutralization of the adduct in a aqueous solution.

The form in which the carbon dioxide is contacted with the alkali metal adduct is not critical to the present invention. The carbon dioxide may be in the form of a pure gas or may be diluted with other gases which are substantially inert toward the trisubstituted borane. Such gases include nitrogen, carbon monoxide, methane, hydrogen, and mixtures of the foregoing. It should be noted that the trisubstituted boranes are extremely sensitive to oxygen and care should be taken to exclude oxygen during the neutralization and the subsequent recovery of the tristubstituted borane.

The neutralization of the adduct in aqueous solution with carbon dioxide precipitates a triarylborane crystal which is larger than that produced by neutralization with known mineral acids. It is also been found that this crystalline filter cake retains less water than cakes obtained by neutralizing with mineral acids. The lower water content of the cake and larger crystals reduce the possibility of hydrolytic degradation during subsequent processing. The use of carbon dioxide also results in a bicarbonate buffered medium which provides high recovery of the desired adduct without over neutralizing and as a result, coprecipitating the over or under phenylated products, e.g., diphenylborinic acid. Control of pH is easier in the presence of the buffer.

The following examples are presented to illustrate but not to restrict the present invention. Parts and precentages are by weight unless otherwise specified.

EXAMPLE 1

An aqueous solution of the sodium hydroxide adduct of triphenylborane was prepared according to the general technique described in Example 3 of U.S. Pat. No. 4,046,815. This solution contained approximately 0.014 g/ml excess sodium hydroxide, 0.033 g/ml of sodium chloride and 0.0348 g/ml of the adduct (measured as triphenylborane). The molar ratio of triphenylborane to diphenylborinic acid in the solution was approximately 2.3. The solution was continuously introduced into a 3 liter agitated vessel at the rate of approximately 16 ml/min while carbon dioxide gas (essentially pure) was introduced beneath the surface of the liquid through a course glass frit at the rate of 600 ml/min (measured at standard conditions). The contents of the vessel were maintained at room temperature and atmospheric pressure while the adduct was fed for approximately 2.8 hours. The flow of carbon dioxide continued for an additional 30 minutes after introduction of the adduct solution was terminated.

The resultant slurry was filtered. Analysis of the filtrate showed that it contained 0.0034 g/ml of triphenylborane with the ratio of triphenylborane to diphenylborinic acid of 0.4. The wet cake from the filtration was then reslurried with approximately 500 ml of water at ambient temperature and again filtered, following which approximately 500 ml of water were poured through the filter cake. Dry nitrogen at ambient temperature was passed through the cake for a period of 24 hours after which time the cake weighed 87.8 g. Analysis of the dry cake indicated 0.34% water, 96% triphenylborane, and a triphenylborane to diphenylborinic ratio of 18. The amount of triphenylborane recovered amounted to 90% of that initially present in the adduct solution.

Carbon dioxide was then passed through the filtrate obtained as set forth above under the conditions and at a rate for the initial neutralization. The solids formed were recovered by filtration and analyzed to shown the presence of 2.75 g of triphenylborane. This amounts to an increase in the overall recovery of approximately 3%.

EXAMPLE 2

An aqueous solution of the sodium hydroxide adduct of triphenylborane was obtained according to the general procedure set forth in Example 3 of U.S. Pat. No. 4,646,815 which solution contained approximately 0.08 g/ml of triphenylborane adduct (measured as triphenylborane). The solution was boiled at atmospheric pressure to obtain a triphenylborane concentration of about 0.15 g/ml. The contents of the flash upon cooling to room temperature yielded two liquid liquid phases and one solid phase. The solids were recovered by filtration and partially dried at room temperature by blowing room temperature nitrogen through the filter cake. Approximately 20 g of the solid obtained was added to 110 ml of 3-pentenenitrile. Small amounts of solids believed to be sodium chloride did not go into the solution and were removed by filtration. The solution was analyzed by Karl Fischer Analysis to contain 1.64% hydroxide content (measured as water). This solution was then passed through a bed of 3A molecular sieve to remove the water introduced with the solids. The analysis of thus treated solution showed it to contain 15.1% adduct. Using the apparatus described in Example 1 carbon dioxide was bubbled through 70 ml (62 g containing 31 millimoles of adduct) of the solution at the rate of 30 ml/min at room temperature and atmospheric pressure for a period of 60 min. This amounts to an excess of carbon dioxide introduced of over 100%. The bicarbonate solids formed were removed by filtration and approximately 10 ml of a solution containing 31 millimoles of triphenylborane were obtained. The amount of triphenylborane represents essentially all of the adduct which was originally present in the solids from evaporation.

We claim:

1. In a process for the recovery of triarylboranes by neutralizing the alkali metal hydroxide salt of said borane, the improvement which comprises using carbon dioxide the effect the neutralization.

2. The process of claim 1, wherein said salt is present in aqueous solution.

3. The process of claim 1 wherein said salt is present in a nonaqueous medium.

4. The process of claim 3 wherein said nonaqueous medium is pentenenitrile.

5. The process for claim 3 wherein said nonaqueous medium is adiponitrile.

6. The process of claims 1, 2, 3, 4 and 5 wherein the arylborane is triphenylborane.

* * * * *